US008644939B2

(12) United States Patent
Wilson et al.

(10) Patent No.: US 8,644,939 B2
(45) Date of Patent: Feb. 4, 2014

(54) METHOD AND DEVICE FOR THE DETECTION, IDENTIFICATION AND TREATMENT OF SLEEP APNEA/HYPOPNEA

(75) Inventors: Willard Wilson, Quebec (CA); Nader Kameli, Hugo, MN (US)

(73) Assignee: Neurostream Technologies General Partnership, Quebec (CA)

( * ) Notice: Subject to any disclaimer, the term of this patent is extended or adjusted under 35 U.S.C. 154(b) by 913 days.

(21) Appl. No.: 12/273,118

(22) Filed: Nov. 18, 2008

(65) Prior Publication Data

US 2010/0125310 A1    May 20, 2010

(51) Int. Cl.
*A61N 1/05* (2006.01)
(52) U.S. Cl.
USPC .......................................................... 607/42
(58) Field of Classification Search
USPC .......................................................... 607/42
See application file for complete search history.

(56) References Cited

U.S. PATENT DOCUMENTS

| 4,289,142 | A | * | 9/1981 | Kearns .......................... 600/529 |
| 5,485,851 | A | * | 1/1996 | Erickson ....................... 600/529 |
| 5,824,027 | A | | 10/1998 | Hoffer et al. |
| 6,587,725 | B1 | | 7/2003 | Durand |
| 6,758,216 | B1 | | 7/2004 | Berthon-Jones et al. |
| 7,117,032 | B2 | | 10/2006 | Childre et al. |
| 7,282,980 | B2 | | 10/2007 | Baru |
| 7,340,302 | B1 | * | 3/2008 | Falkenberg et al. ............... 607/9 |
| 7,672,728 | B2 | * | 3/2010 | Libbus et al. .................. 607/42 |

| 2005/0085866 | A1 | 4/2005 | Tehrani |
| 2005/0131288 | A1 | 6/2005 | Turner et al. |
| 2006/0189881 | A1 | 8/2006 | Fassio |
| 2006/0224211 | A1 | 10/2006 | Durand et al. |
| 2007/0150006 | A1 | 6/2007 | Libbus et al. |
| 2008/0065184 | A1 | 3/2008 | Hoffer et al. |
| 2010/0016908 | A1 | 1/2010 | Martin et al. |
| 2010/0125310 | A1 | 5/2010 | Wilson et al. |
| 2010/0312302 | A1 | 12/2010 | Zealear |
| 2011/0190642 | A1 | 8/2011 | Alt et al. |

FOREIGN PATENT DOCUMENTS

| WO | 2002066111 A1 | 8/2002 |
| WO | 2008005903 | 1/2008 |
| WO | 2008025155 A1 | 3/2008 |
| WO | 2008046190 A1 | 4/2008 |
| WO | 2011016864 A1 | 2/2011 |

OTHER PUBLICATIONS

Bevan; "Tonically Active Vagal Pulmonary Afferent Neurones"; Life Sciences, Pergamon Press, Oxford, GB; vol. 4; No. 23; Dec. 1, 1965; pp. 2289-2294.
Page M and Jeffery HE, Airway protection in sleeping infants in response to pharyngeal fluid stimulation in the supine position, Pediatr Res, 1998, pp. 691-698, vol. 44, No. 5.
Dua KS et al, Safety and feasibility of evaluating airway-protective reflexes during sleep: new technique and preliminary results, Gastrointest Endosc, 2007, pp. 483-486, vol. 65, No. 3.

(Continued)

*Primary Examiner* — George Manuel
(74) *Attorney, Agent, or Firm* — Polsinelli PC

(57) ABSTRACT

A method and device for treating sleep apnea and sleep hypopnea by monitoring respiratory-related activity from the internal branch of the superior laryngeal nerve, interpreting these internal signals to detect and classify apnea events, and stimulating nerves or muscles to elicit appropriate corrective responses to adverse respiratory events.

100 Claims, 9 Drawing Sheets

(56) References Cited

OTHER PUBLICATIONS

Dozier, TS et al, Coordination of swallowing and respiration in normal sequential cup swallows, Laryngoscope, 2006, pp. 1489-1493, vol. 116.
Gheshmy A, et al, Chronic hypercapnia modulates respiratory-related central pH/CO2 chemoreception in an amphibian, Bufo marinus, J. Exper Biol, 2006, pp. 1135-1146, vol. 209.
Jobin V et al, Swallowing function and upper airway sensation in obstructive sleep apnea, J. Appl Physiol, 2007, pp. 1587-1594, vol. 102.
Teramoto, S et al, Impaired Swallowing Reflex in Patients With Obstructive Sleep Apnea Syndrome, Chest, 1999, pp. 17-21, vol. 116.
Weaver TE and Grunstein RR, Adherence to Continuous Positive Airway Pressure Therapy, The Challenge to Effective Treament, Proc Am Thorac Soc, 2008, pp. 173-178, vol. 5.
International Search Report regarding PCT/US2011/36653 issued Aug. 26, 2011, 17 pages.
International Search Report regarding PCT/CA2007/001784 issued Jan. 28, 2008, 6 pages.
Supplemental Search Report regarding EP07855411.0 issued Jul. 11, 2011, 10 pages.
International Search Report regarding PCT/CA2008/002036 issued Jul. 28, 2009, 3 pages.
International Search Report and Written Opinion for PCT/US13/23488 mailed Jun. 14, 2013 (18 pages).

* cited by examiner

METHOD AND DEVICE FOR THE DETECTION, IDENTIFICATION AND TREATMENT OF SLEEP APNEA/HYPOPNEA

TECHNICAL FIELD

The present invention relates to a method and device for the detection, identification and treatment of sleep apnea/hypopnea.

BACKGROUND

Sleep apnea/hypopnea affects around 5% of the adult U.S. population. Its short-term effects consist of complete (apnea) or partial (hypopnea) termination of airflow, decreased oxygen in the blood, increased $CO_2$ in the blood, interrupted sleep, and excessive daytime sleepiness. Long-term effects may include hypertension, diabetes, heart attack, stroke, arrhythmia and brain damage.

The principal forms of sleep apnea are: 1) obstructive sleep apnea (OSA), characterized by a physical blockage of the upper airway during sleep, 2) central sleep apnea (CSA), caused by a decreased central respiratory drive during sleep, and 3) mixed sleep apnea, which includes components of both OSA and CSA. OSA is the most common and dangerous of all sleep-related breathing disorders. While CSA is uncommon in its pure form, it is prevalent in patients with congestive heart failure, as a component of Cheyne-Stokes respiration.

The obstructive component in OSA is related to decreased tone in the upper airway as the muscles relax during sleep. During normal respiration, upper airway patency is maintained by the negative pressure reflex, which activates pharyngeal dilators in response to negative transthoracic pressure during inspiration. In apneic patients, the negative pressure reflex is insufficient to maintain patency during sleep. Here, the negative pressure created during inspiration is sufficient to constrict or collapse the lumen of the flaccid airway.

The treatment of choice for sleep apnea is continuous positive air pressure (CPAP). Basically, CPAP maintains an open airway by inflating it with pressurized air through a nose or face mask. Used properly, CPAP is 100% effective for treating OSA. Although CSA has a neurological origin, it has also been successfully treated with positive air pressure. Despite its efficacy, however, CPAP treatment is poorly tolerated by sleep apnea patients. In one recent survey, CPAP non-compliance (less than 4 h/night) was reported in between 46% and 83% of patients [1]. Reasons for non-compliance include discomfort, claustrophobia, pressure sores, dry nose or mouth, and machine noise.

The most common alternative to CPAP is a surgical removal of the uvula, caudal soft palate, and tonsils. This procedure has a success rate of about 50%. Other surgical treatments, such as tongue reduction, advancement of the tongue, tracheostomy, or implants to stiffen the soft palate have limited benefit relative to their invasiveness, risk, and irreversibility. Non-surgical approaches such as weight loss, medication, changes in sleeping position or dental appliances also suffer from limited effectiveness or compliance.

Implantable medical devices are currently under investigation as a method to detect and/or treat sleep apnea. Such devices are similar in their general design to cardiac pacemakers and share in many of the advantages of this mature technology.

With regard to detection, implantable devices have been described that detect apnea by monitoring the bioelectric activity of the diaphragm, intercostal muscles, or their efferent nerves. Other devices monitor the bioelectric activity of upper airway muscles or their efferent nerves. Still others monitor implanted sensors for indications of, for example, thoracic pressure or blood oxygenation.

With regard to treatment, implantable devices have been described that terminate apnea using drug delivery, atrial overdrive pacing or electrical stimulation of the nerves or muscles that control respiratory activities. For OSA, electrical stimulation has been described that maintains patency by activating upper airway muscles or the efferent nerves controlling them. For CSA, treatments that elicit breathing by electrically stimulating the diaphragm, intercostal muscles, or their efferent nerves have been described.

SUMMARY

According to an illustrative embodiment of the present invention, there is provided a method for monitoring the respiratory activity of a subject, comprising the steps of:
  recording an electroneurogram signal from the internal branch of the superior laryngeal nerve of the subject;
  conditioning the electroneurogram signal;
  computing an index of respiratory activity of the conditioned electroneurogram signal; and
  reporting an occurrence of an apneic event when the index of respiratory activity meets at least one apnea criteria.

According to another illustrative embodiment of the present invention, the method further comprising the step of generating a stimulation signal which acts to increase airway patency or stimulate breathing following the reporting of the apneic event.

According to yet another illustrative embodiment of the present invention, the index of respiratory activity is computed by applying a rectification and bin-integration algorithm to the conditioned electroneurogram signal.

According to a further illustrative embodiment of the present invention, the at least one apnea criteria includes a first criteria associated with obstructive sleep apnea and a second criteria associated with central sleep apnea, and wherein the reporting step includes reporting the apneic event as an obstructive sleep apnea event when the index of respiratory activity meets the first criteria and as a central sleep apnea event when the index of respiratory activity meets the second criteria.

According to a further still illustrative embodiment of the present invention, the method further comprises the step of reporting an occurrence of an obstructive sleep hypopnea event when the index of respiratory activity meets a third criteria associated with obstructive sleep hypopnea and reporting an occurrence of a central sleep hypopnea event when the index of respiratory activity meets a fourth criteria associated with central sleep hypopnea.

According to another illustrative embodiment of the present invention, there is provided a method for treating sleep apnea and/or hypopnea of a subject, comprising eliciting a reflexive pattern activity from the central nervous system of the subject following the detection of the sleep apnea event.

According to a further illustrative embodiment of the present invention, the reflexive pattern activity is swallowing and is elicited by stimulating the internal branch of the superior laryngeal nerve or the glossopharyngeal nerve with an electrical signal at a rate of about 20 Hz to 50 Hz.

According to another illustrative embodiment of the present invention, there is provided a system implementing the above described methods.

BRIEF DESCRIPTION OF THE DRAWINGS

Non-limiting illustrative embodiments of the invention will now be described by way of example only with reference to the accompanying drawings, in which.

DETAILED DESCRIPTION

Generally stated, the non-limitative illustrative embodiment of the present invention provides a method and device for treating sleep-related breathing disorders such as sleep apnea/hypopnea by monitoring respiratory-related activity from nerve or muscle, interpreting these internal signals to detect and classify adverse events in the airway, and stimulating nerves or muscles to elicit appropriate corrective responses to adverse respiratory events.

In the detailed description, unless specified otherwise, reference to the term "apnea" is defined to mean either an obstructive, central, mixed, or complex episode of apnea or hypopnea, occurring during sleep or awake as in Cheyne-Stokes respiration.

Normal Respiration

Figure 1:
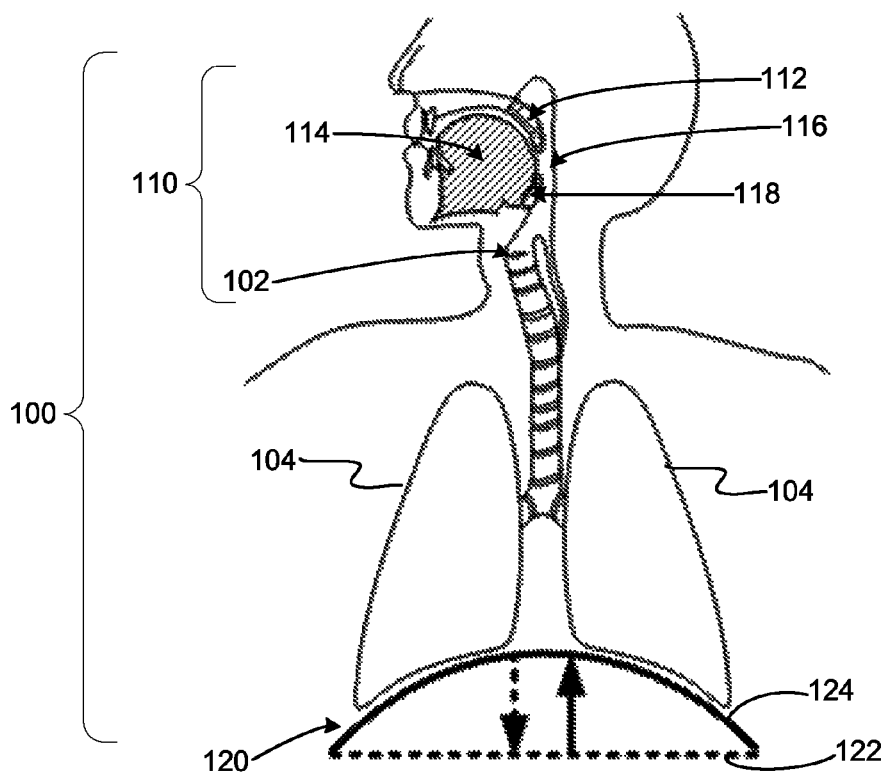
FIG. 1 is a schematic representation of the human airway relevant to upper airway pressure as measured at the larynx during normal respiration.

Referring to FIG. 1, there is shown a schematic representation of the human airway 100 relevant to upper airway 110 pressure as measured at the larynx 102 during normal respiration. During normal inspiration, the diaphragm and intercostal muscles 120 contract 122, creating a negative pressure in the airway 100 and drawing air into the lungs 104. Expiration is typically passive, resulting from relaxation of the diaphragm and intercostal muscles 120 back to their resting position 124, and elastic recoil of the lungs 104. The amount of air flow produced by changing airway 100 pressure is influenced by resistance from the structures of the upper airway 110, including the soft palate 112, tongue 114, pharynx 116, and epiglottis 118.

Figure 2:
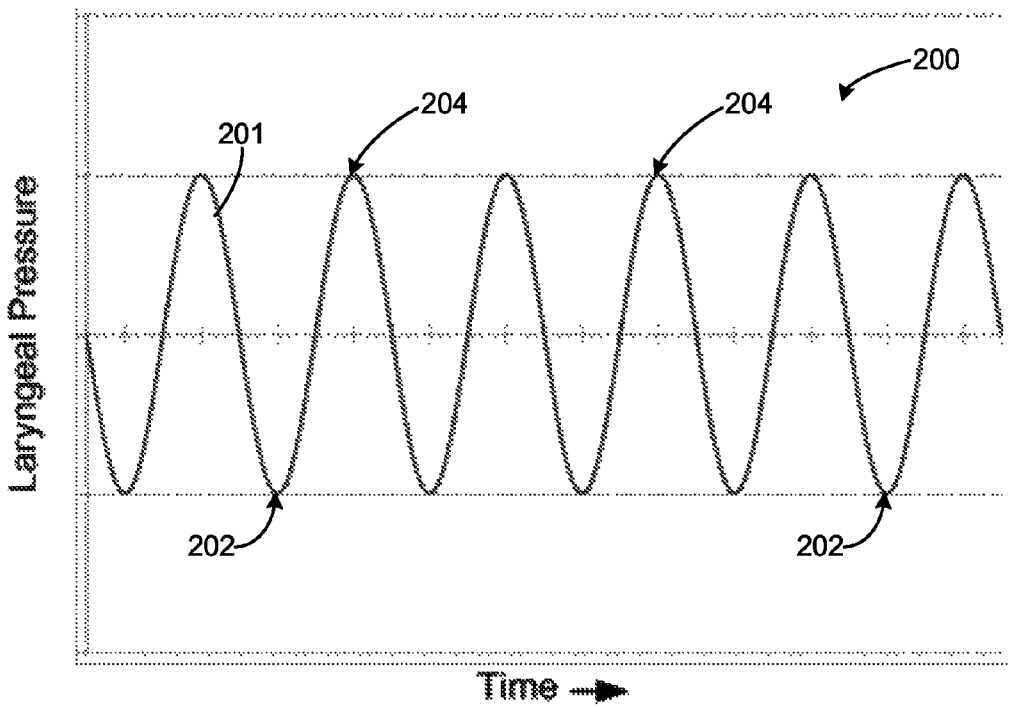
FIG. 2 is a graph of airway pressure measured at the larynx during the normal breathing process.

FIG. 2 shows a graph 200 of airway pressure 201 measured at the larynx 102 (see FIG. 1) during the normal breathing process, comprising regular inspiration 202 and expiration 204 peaks of similar amplitude and frequency. Airway pressure at the larynx 102 is transduced by mucosal mechanoreceptors that are sensitive to pressure and is communicated to the central nervous system via the internal branch of the superior laryngeal nerve (iSLN).

Respiration During an OSA Event

Figure 3:
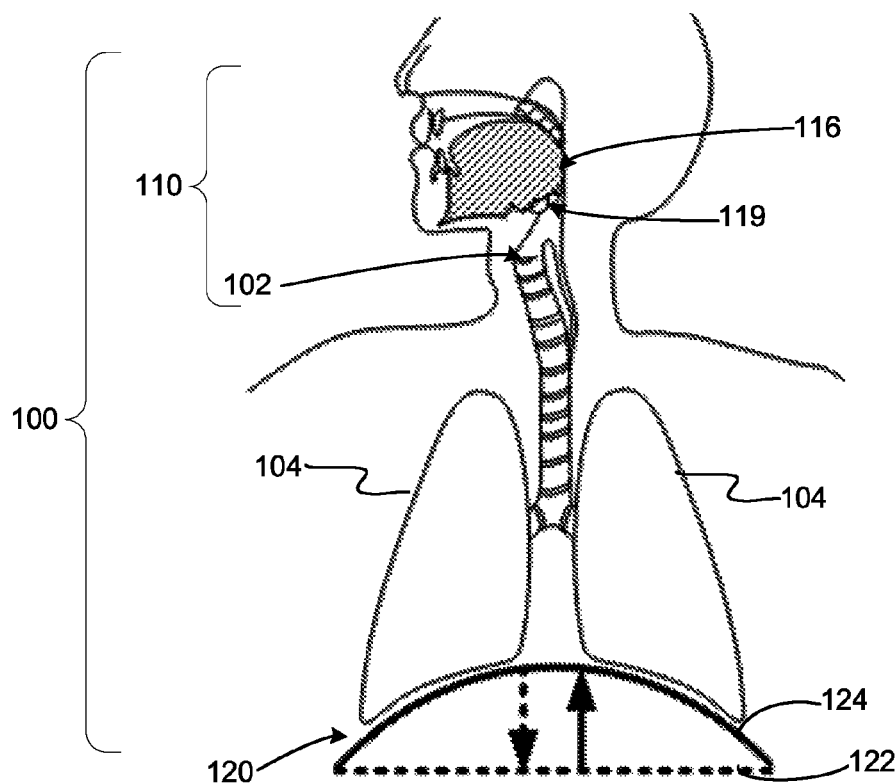
FIG. 3 is a schematic representation of the human airway relevant to upper airway pressure as measured at the larynx during an obstructive sleep apnea (OSA) event.

Referring to FIG. 3 there is shown a schematic representation of the human airway 100 relevant to upper airway pressure as measured at the larynx during an OSA event. Here, a lack of muscle tone in the upper airway 110 allows pharyngeal structures 116 to partially or completely block the lumen 119 of the airway 100, particularly when subjects sleep on their back. Respiratory drive continues during the OSA event, the diaphragm and intercostal muscles 120 contract 122, creating a negative pressure in the airway 100 drawing flaccid pharyngeal structures 116 into the airway lumen 119.

Figure 4:
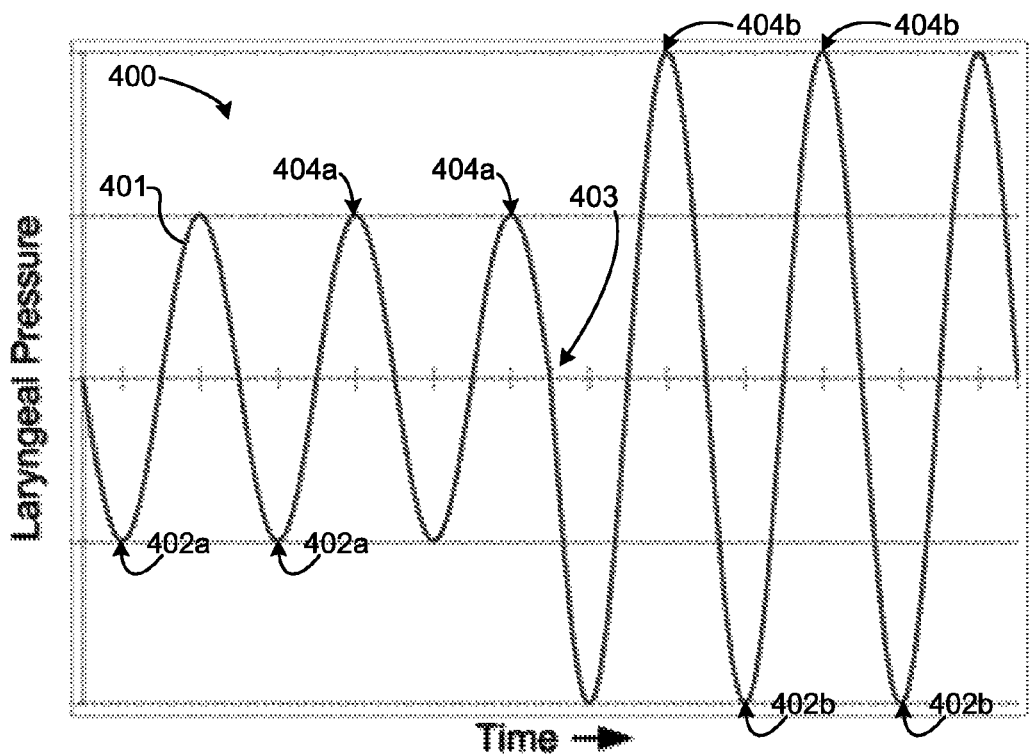
FIG. 4 is a graph of airway pressure measured at the larynx at the outset of an OSA event.

FIG. 4 shows a graph 400 of airway pressure 401 measured at the larynx 102 (see FIG. 3) at the outset of an OSA event, comprising normal breathing process inspiration 402a and expiration 404a peaks before the OSA event and then inspiration 402b and expiration 404b peaks of a greater amplitude during the OSA event. This increase in the amplitude of the airway pressure 401 reflects continuing attempts on the part of the subject to breathe after airway obstruction, generating greater than normal airway pressures 401. The outset of the OSA event 403 can then be identified by the sudden increase in amplitude of the inspiration 402 and expiration 404 peaks of the airway pressure 401.

Respiration During a CSA Event

Figure 5:
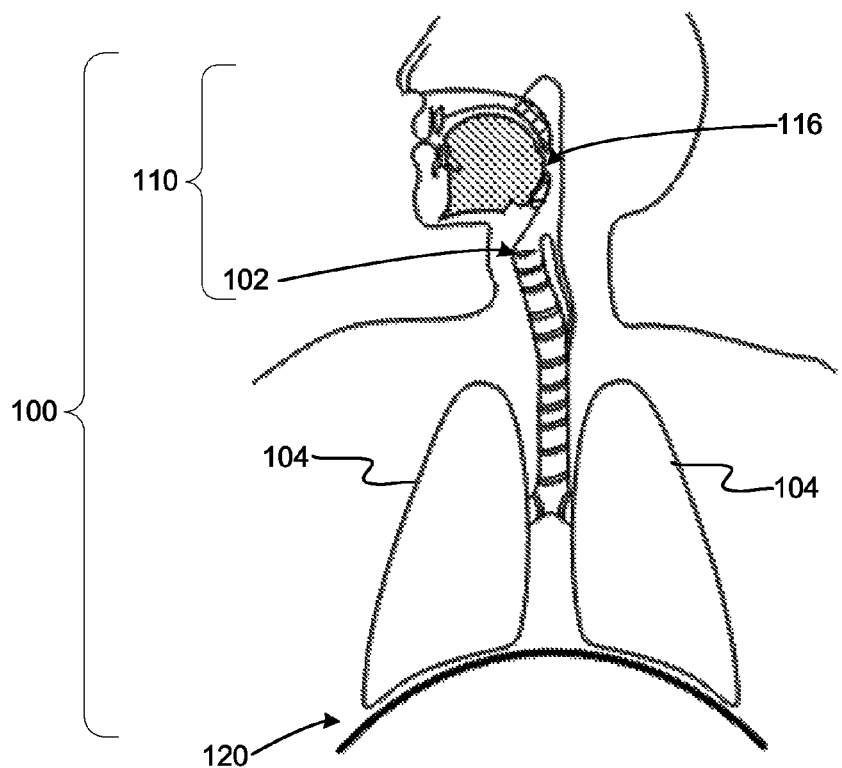
FIG. 5 is a schematic representation of the human airway relevant to upper airway pressure as measured at the larynx during a central sleep apnea (CSA) event.

Referring to FIG. 5, there is shown a schematic representation of the human airway 100 relevant to upper airway pressure as measured at the larynx during a CSA event. Here, the upper airway 110 remains open, but diminished central respiratory drive reduces or eliminates diaphragm 120 movement, and thus air flow during the CSA event.

Figure 6:
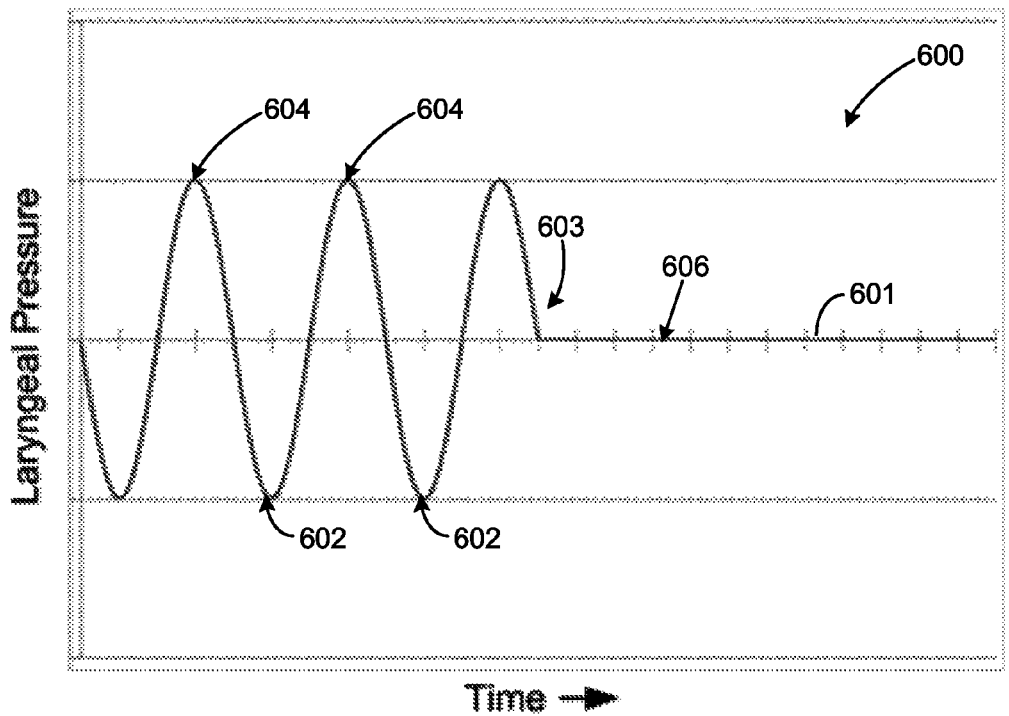
FIG. 6 is a graph of airway pressure measured at the larynx at the outset of a CSA event.

FIG. 6 shows a graph 600 of airway pressure 601 measured at the larynx 102 (see FIG. 5) at the outset of a CSA event, comprising normal breathing process inspiration 602 and expiration 604 peaks before the CSA event and then an absence of, or very low amplitude, inspiration and expiration peaks 606 during the CSA event. Despite a patent upper airway 110, upper airway pressure 601 is not fully modulated after the onset of the CSA event and diminution of diaphragm movement. The outset of the CSA event 603 can then be identified by the sudden drop 606 in the amplitude of the inspiration 602 and expiration 604 peaks of the airway pressure 601.

Detection and Classification of Apnea Events

Figure 7:
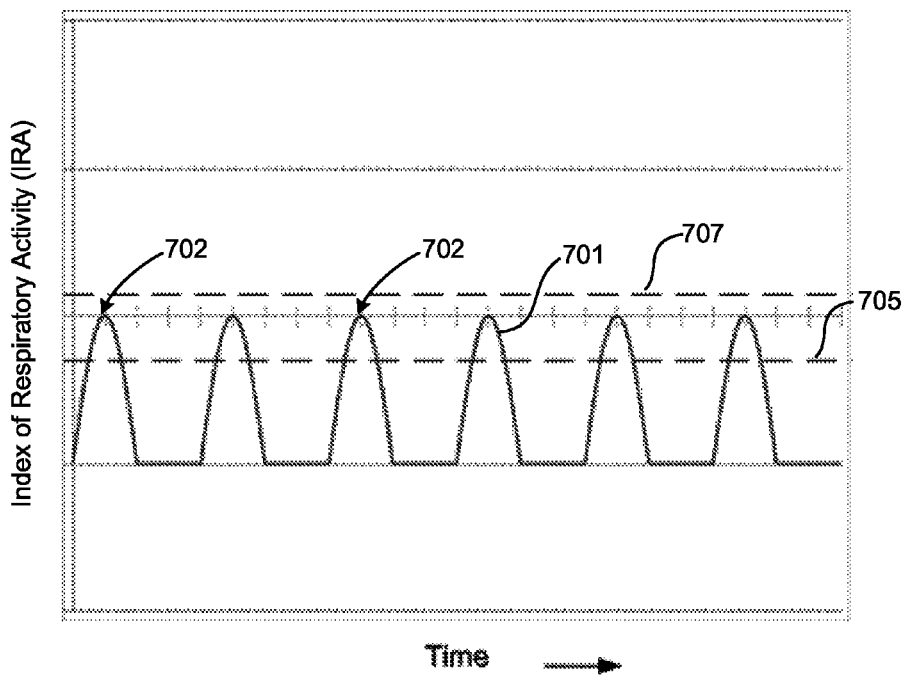
FIG. 7 is a graph of an index of respiratory activity (IRA) computed from the rectified and bin-integrated (RBI) electroneurogram of the iSLN during normal respiration.

It has been discovered that the electroneurogram (ENG) of the internal branch of the superior laryngeal nerve (iSLN) is correlated with pressure in the upper airway 110 (see FIG. 1). This relationship can be demonstrated by calculating an index of respiratory activity (IRA) that is indicative of the amplitude and timing of the ENG signal. For example, the IRA may be calculated by applying a rectification and bin-integration (RBI) algorithm to the amplified iSLN signal. Referring to FIG. 7, during normal breathing, each peak 702 of the IRA 701 calculated using this method corresponds to a regular inspiration peak 202 of the airway pressure 201 measured at the larynx 102, as illustrated in FIG. 2.

The amplitude of peaks in the IRA during each breath occurs within a normal range of amplitudes which may be determined using a calibration process during normal respiration of a given subject using, for example, polysomnographic techniques. This range of amplitudes can be used to set upper 707 and lower 705 thresholds for apnea event detection. Peaks 702 outside of this normal range can be detected using simple fixed-level thresholds and defined as apneic events.

The upper 707 and lower 705 thresholds can further be used to classify, in real-time, a detected apneic event as being either an OSA event or a CSA event.

It is to be understood that although the above the IRA is calculated by applying a rectification and bin-integration (RBI) algorithm to the amplified iSLN signal, other signal processing algorithms may also be applied to calculate the IRA including: high pass filter, low pass filter, bandpass filter, notch filter, FIR filter, IIR filter, smoothing, moving average, Wiener (optimal) filter, rectification, bin-integration, multi-channel noise reduction, principal components analysis, independent components analysis, wavelet analysis, Fourier transformation, matched filtering, variance/variance ratio calculations, or some combination of the above. The raw iSLN ENG waveform may also be used directly. IRAs based on neural network analyses, cluster analysis in multidimensional feature space, cluster cutting using k-means, Bayesian expectation-maximization, closest centers, or manual cluster cutting methods may also be used.

It is to be also understood that an IRA could be computed from any number of other iSLN ENG signal features that vary with respiratory state such as event or waveform timing, interval, amplitude, duration, rise time, fall time, slope, presence, absence, pattern, 1st derivative, 2nd derivative, 3rd derivative, root mean square amplitude, peak-to-peak amplitude, variance, statistical probability or probability relative to baseline or running average.

It is also to be understood that detection of respiratory events in the IRA using methods other than fixed-level thresholding may be used, for example noise-tracking or other adaptive thresholds, energy or non-linear energy thresholds, or any variety of other detection operations on the raw or processed data.

OSA Event

Figure 8:
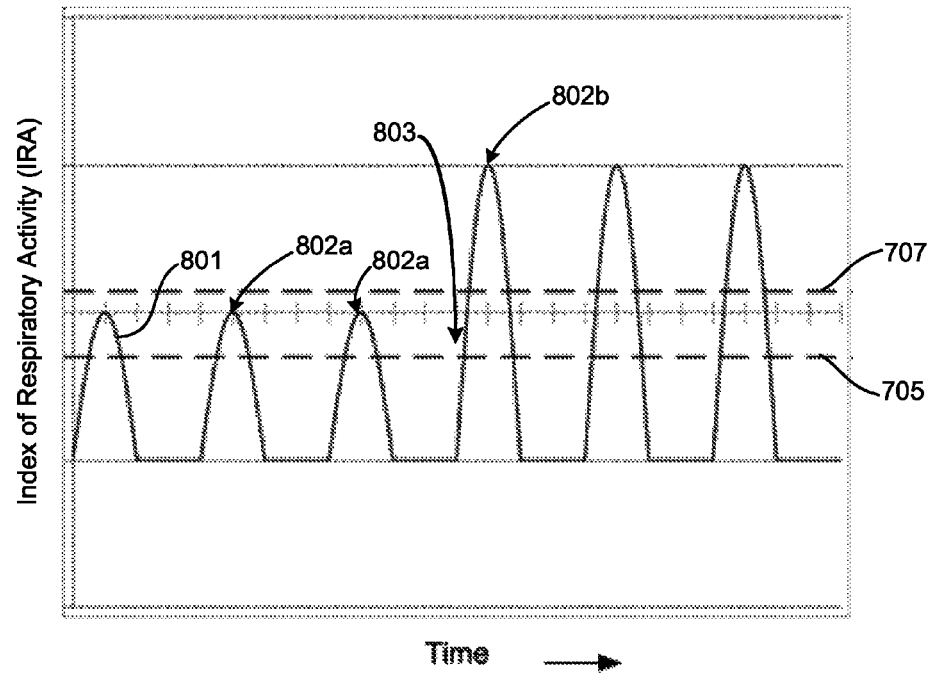
FIG. 8 is a graph of an index of respiratory activity (IRA) computed from an RBI electroneurogram of the ISLN at the outset of an OSA event.

Referring to FIG. 8, there is shown an example of peaks 802 of the IRA 801 at the outset of an OSA event, comprising normal breathing process inspiration related peaks 802a within the upper 707 and lower 705 thresholds before the OSA event and then inspiration related peaks 802b of an amplitude greater than the upper 707 threshold during the OSA event. The outset of the OSA event 803 can then be identified by the first crossing of the upper 707 threshold by the inspiration related peaks 802.

Figure 9:
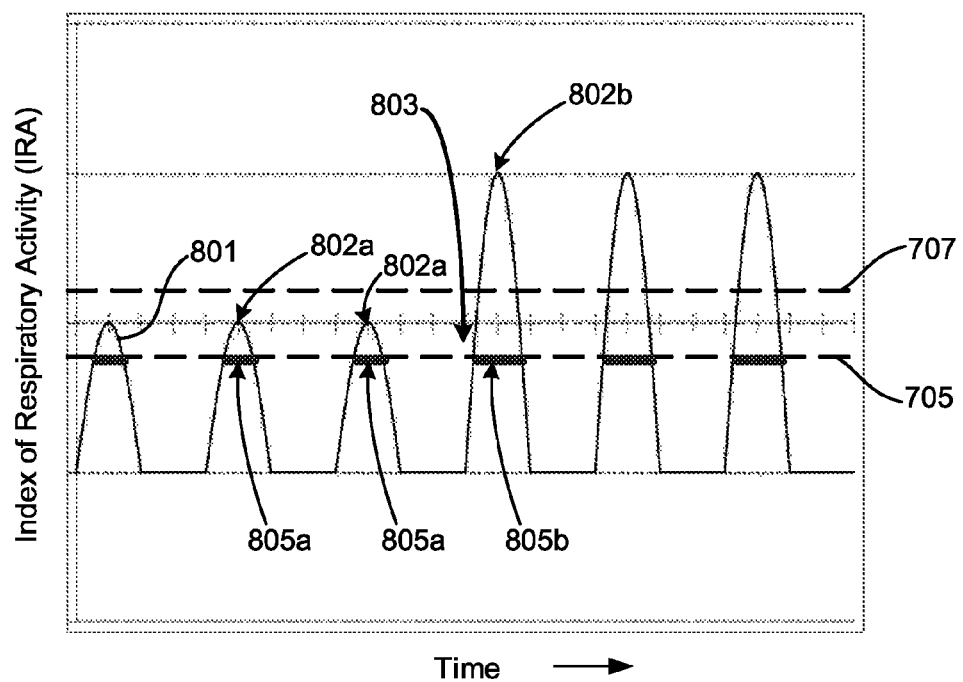
FIG. 9 is a graph of the index of respiratory activity (IRA) of FIG. 8 showing an alternative way of identifying the occurrence of an OSA event using a measure of peak durations.

Alternatively, referring to FIG. 9, it may be observed that at the outset of the OSA event 803 the durations 805b of the peaks 802b of the RBI ENG measured at a fixed level, for example threshold 705, are greater than the peak durations 805a of the peaks 802a measured during the normal breathing process. Accordingly, the peak durations of the RBI ENG may be used to identify the outset of an OSA event by setting an appropriate threshold.

Figure 10:
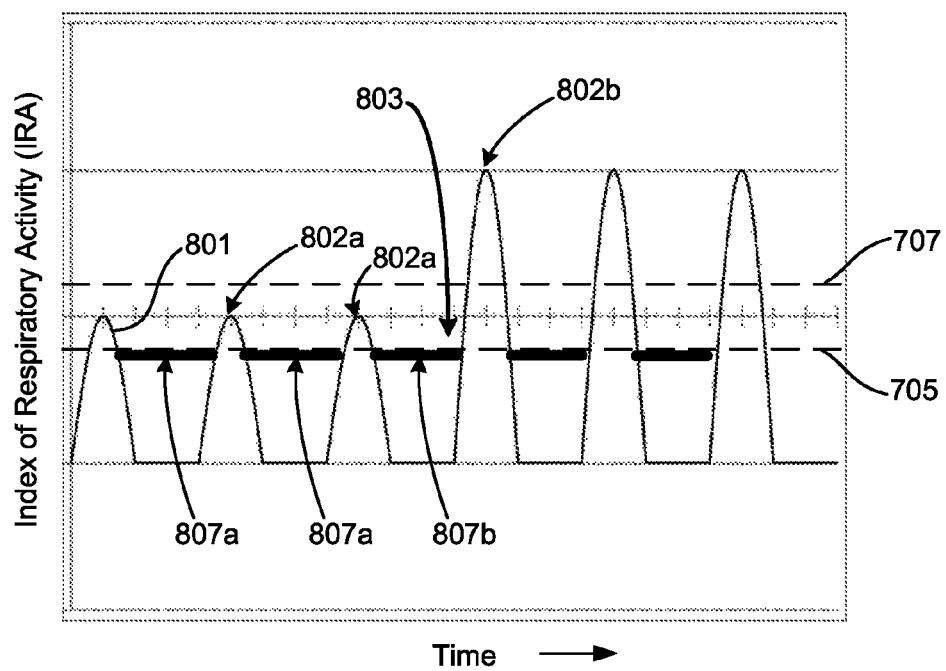
FIG. 10 is a graph of the index of respiratory activity (IRA) of FIG. 8 showing another alternative way of identifying the occurrence of an OSA event using a measure of interpeak intervals.

Similarly, referring to FIG. 10, it may be observed that at the outset of the OSA event 803 the intervals 807b between the peaks 802b of the RBI ENG measured at a fixed level, for example threshold 705, are smaller than the interpeak intervals 807a between the peaks 802a measured during the normal breathing process. Accordingly, the interpeak intervals of the RBI ENG may be used to identify the outset of an OSA event by setting an appropriate threshold.

CSA Event

Figure 11:
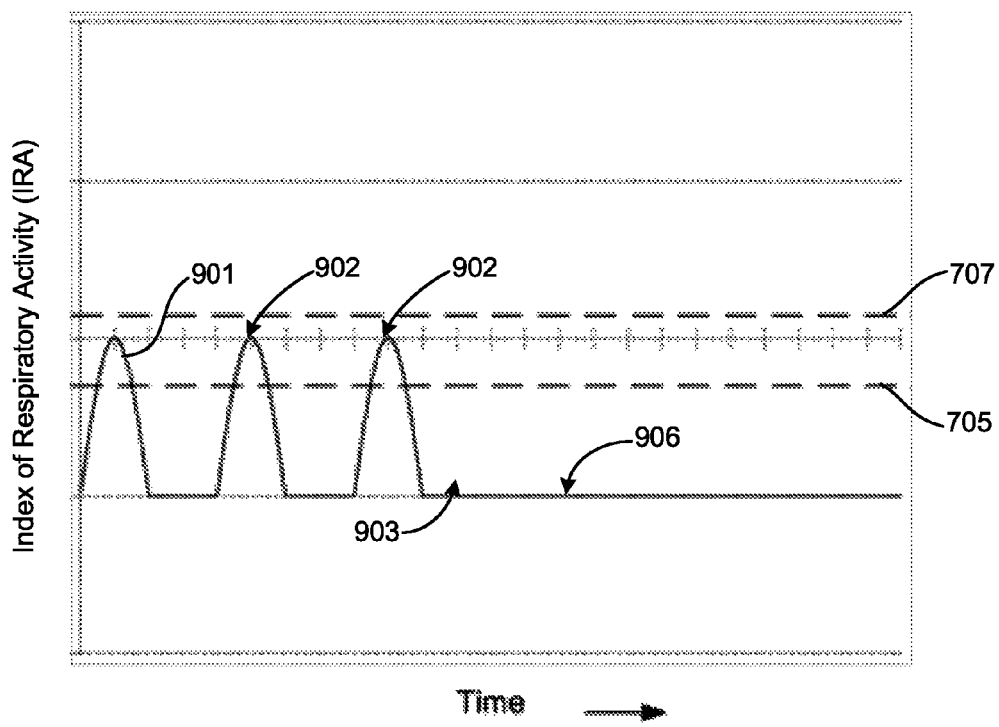
FIG. 11 is a graph of an index of respiratory activity (IRA) computed from an RBI electroneurogram of the iSLN at the outset of a CSA event.

Referring to FIG. 11, there is shown an example of peaks 902 of the IRA 901 at the outset of a CSA event, comprising normal breathing process inspiration related peaks 902 within the upper 707 and lower 705 thresholds before the CSA event and then inspiration related peaks 906 of an amplitude lower than the lower 705 threshold (or absence of peaks) during the CSA event. The outset of the CSA event 903 can then be identified by the first absence of crossing of the lower 705 threshold by the inspiration related peaks 902 for a set time period. This period of time may be set to represent the average time between one or more respiration cycle.

As is the case with OSA events (see FIGS. 9 and 10), other IRAs may be calculated in order to identify CSA events, such as the peak durations and interpeak intervals of the RBI ENG by setting appropriate levels and thresholds. It is to be understood that the absence of measurements at a specified level may indicate a CSA event.

Apnea Event Severity

In an alternative embodiment, the severity of the apnea event may be determined by comparing the amplitude of the apneic IRA 801, 901 to that observed during normal breathing 701. More severe apnea is characterized by IRA peaks 802, 902 having amplitudes far from the upper 707 and lower 705 thresholds, while less severe apnea or hypopnea is characterized by IRA peaks 802, 902 having amplitudes just above or below the upper 707 and lower 705 thresholds. The level of apnea thus determined can be used to adjust the parameters and characteristics of the applied neurostimulation treatment. This may include changing the stimulation waveform, increasing or decreasing the stimulus amplitude, increasing or decreasing the number of stimuli delivered, selecting electrodes in specific locations or changing the number of stimulation electrodes used.

Figure 12:
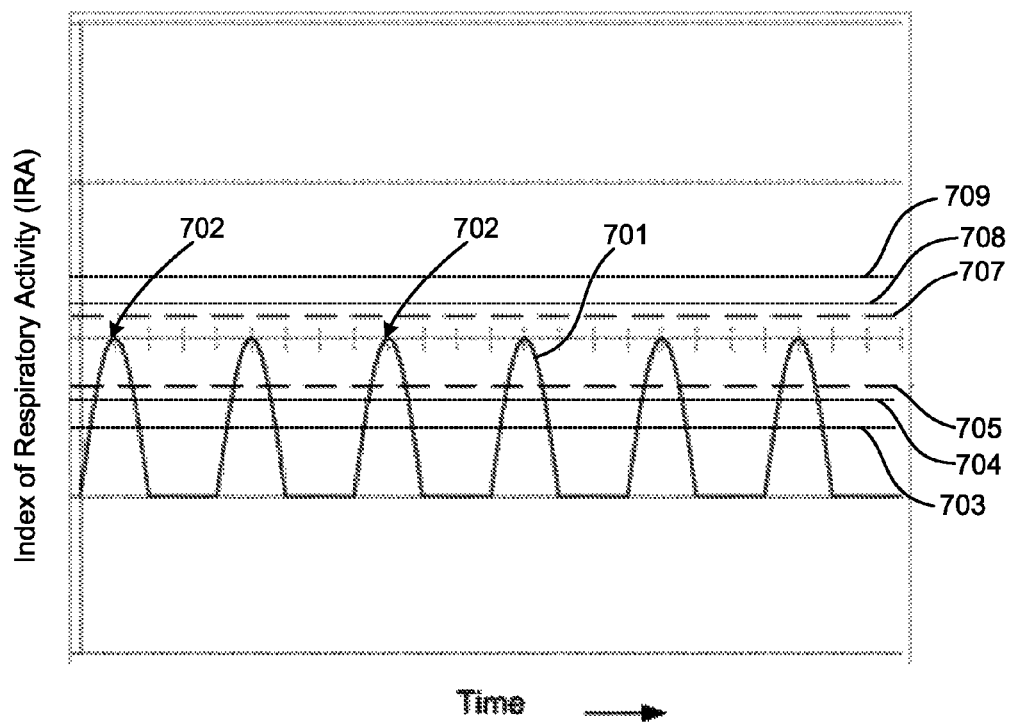
FIG. 12 is a graph of an index of respiratory activity (IRA) computed from the rectified and bin-integrated (RBI) electroneurogram of the iSLN during normal respiration showing multiple apnea severity levels.

For example, referring to FIG. 12, various OSA 708, 709 and CSA 704, 703 severity levels may be assigned corresponding thresholds. It is to be understood that the number of OSA and CSA severity levels may vary depending on the precision of the circuitry and/or algorithm used.

Hypopnea

In a further alternative embodiment, apneic events may be further identified as OSA or obstructive sleep hypopnea (OSH) as well as CSA or central sleep hypopnea (CSH). For example, referring still to FIG. 12, the interval between thresholds 707 and 708 may be associated with OSH while threshold 708 may be associated with OSA, meaning that IRA peaks between thresholds 707 and 708 are identified as OSH while IRA peaks above threshold 708 are identified as OSA. Conversely, the interval between thresholds 705 and 704 may be associated with CSH while threshold 704 may be associated with CSA, meaning that IRA peaks between thresholds 705 and 704 are identified as CSH while IRA peaks below threshold 704 are identified as CSA. The range of values for which IRA peaks are defined as OSH as opposed to OSA, as well as CSH as opposed to CSA, may be determined using a calibration process during abnormal respiration of a given subject using, for example, polysomnographic techniques.

It is to be understood that OSH, OSA, CSH and CSA may be subdivided into multiple severity levels depending on the precision of the circuitry and/or algorithm used.

As described above for the OSA and CSA event detection, the variation in IRAs calculated using algorithms other than RBI ENG may also be used to determine the severity of the apneic or hypopneic event.

Although peaks in the IRA coincident with negative pressure receptor activity are described above, it is to be understood that receptors sensitive to other stimuli and modalities, respiratory events, phases or features, and with afferents carried by other nerves may also used. This is meant to include mechanoreceptors sensitive to positive airway pressure, stretch, position, shear or slip, vibration, texture, touch, touch and pressure, muscle stretch, muscle "drive", air flow, blood pressure or osmolarity; chemoreceptors sensitive to $CO_2$, $O_2$, or pH; thermoreceptors sensitive to temperature or airflow; nociceptors sensitive to polymodal pain, or some combination of the above.

Apneic Event Detection, Identification and Treatment

Figure 13:
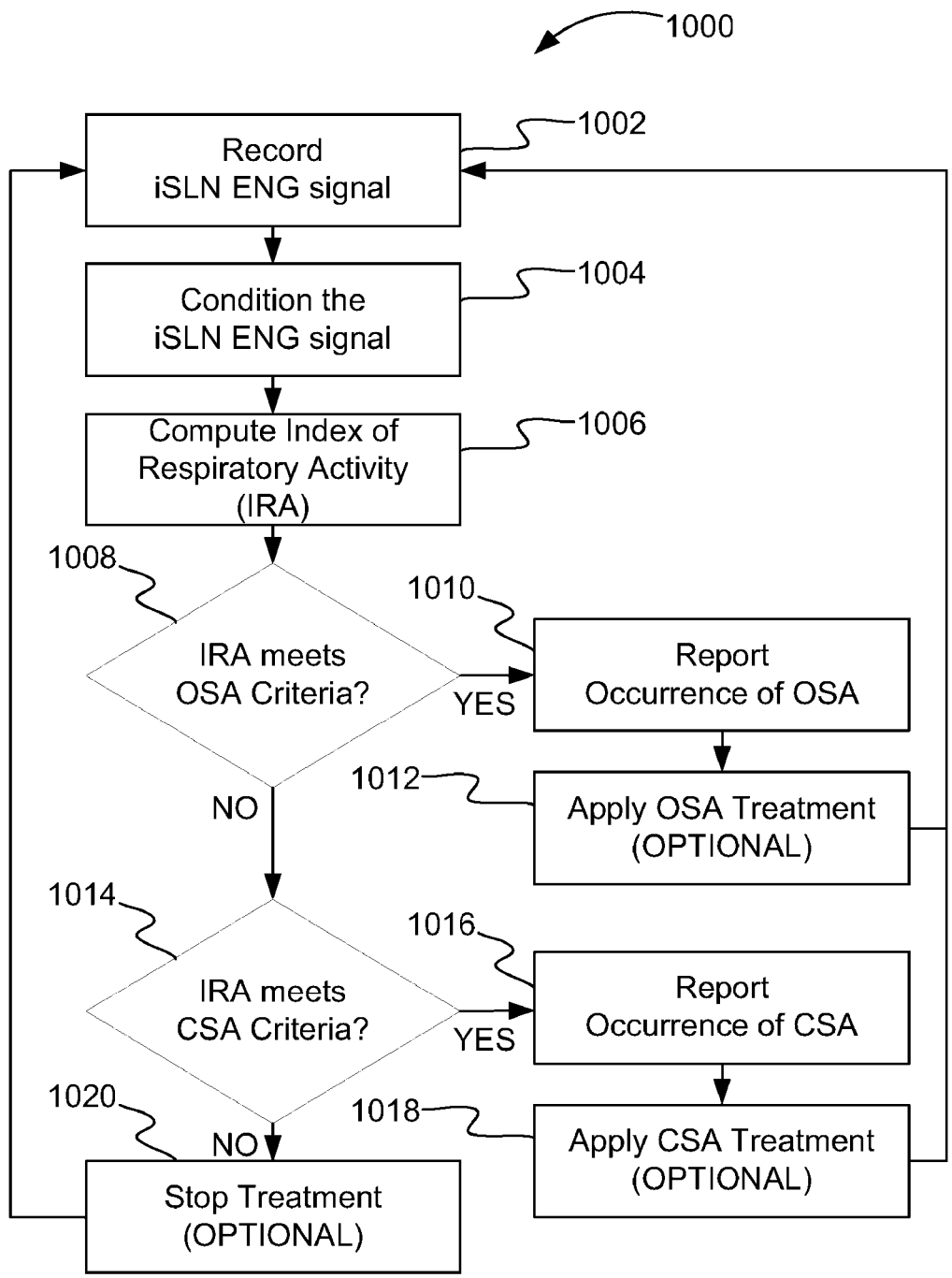
FIG. 13 is a flow diagram depicting the detection, identification and treatment of sleep apnea process in accordance with a first illustrative embodiment of the present invention.

Referring to FIG. 13, there is shown in a flow diagram a process 1000 for the detection and classification of apnea events in accordance with a first illustrative embodiment of the present invention. The steps composing the process are indicated by blocks 1002 to 1020.

The process 1000 starts at block 1002, where the iSLN ENG signal is recorded, after which, at block 1004, the iSLN ENG signal is conditioned (for example amplified).

At block 1006, an index of respiratory activity (IRA) is computed. The IRA is a measure of the iSLN ENG signal which varies with the respiratory activity of the subject and may be used to detect sleep apnea events through comparison with thresholds associated with normal respiratory activity. For example, the IRA may be the amplitude envelope computed by applying an RBI algorithm to the filtered and amplified iSLN ENG signal. This algorithm first rectifies the iSLN ENG signal and then sums the result in bins, essentially applying a low pass filter to the rectified signal. Alternatively, the IRA may be the root-mean-square or peak-to-peak amplitude of the iSLN ENG signal, the duration of peaks in the RBI iSLN ENG signal measured at a fixed level or the interval between peaks of the RBI iSLN ENG signal measured at a fixed level.

Optionally, a moving average filter may then be applied to the IRA, for example a moving average filter spanning one second of data, and the result optimized using, for example, the solution to the Wiener-Hopf equation. The moving average filter helps to reduce the influence of variability inherent to iSLN ENG signals and its total length may be selected so as to be near the smallest feature (peak width) to be detected.

At block 1008, the process 1000 verifies if the IRA meets the criteria defining OSA. For example, in the case where the IRA is the RBI ENG of the iSLN signal, OSA is defined as peak values exceeding the upper threshold 707 of the range of amplitudes observed during normal respiration as illustrated in FIG. 7. It is to be understood that the criteria defining OSA will vary depending on the IRA used.

If the IRA meets the criteria of OSA, the process 1000 proceeds to block 1010 where an OSA event is reported. Then, optionally, at block 1012, airway opening stimulation may be triggered in response to the detection of the OSA event.

The airway opening stimulation acts to replace or augment the airway patency during inspiration. The stimulation may take a number of different forms and is designed to remain below the arousal threshold of the sleeping subject. Possible targets for stimulation include specific nerves that control upper airway patency such as, for example, the hypoglossal or glossopharyngeal nerves, or their combination. Likewise, direct stimulation of specific muscles that control upper airway patency such as, for example, genioglossus, tensor palatini, or sternohyoid muscles, or their combination, can also be used. Treatment can be accomplished by applying stimulation individually to some or all of the muscles involved in airway patency, or individually to the nerves efferent to these muscles, or some combination of the thereof. Stimulation of activities or muscles or nerves that increases upper airway patency can be delivered phasically, in synchrony with inspiration, or tonically throughout the entire respiratory cycle.

In an alternative embodiment, the stimulation may be aimed at eliciting reflexive and pre-programmed coordinated activity from swallow-related central pattern generators in the central nervous system. For example, the iSLN can be electrically stimulated at a rate of about 20 Hz to 50 Hz in order to provoke a swallowing reflex. Similar stimulus protocols give rise to one or more complete sequences of pharyngeal swallow. During pharyngeal swallow, upper airway pressure increases from negative values up to atmospheric pressure, the muscles of larynx and pharynx are activated, and the pharynx and larynx close and then open. The entire coordinated pattern of pharyngeal muscle activation ends with an open pharynx. Stimulation of this pattern is designed to open a collapsed upper airway and restore airway patency. Stimulation of other patterned activities may also be used to increase airway patency, such as the negative pressure reflex, cough, yawn, gag, etc., as well as some combination of stimulated patterned activities. Stimulation of the swallow sequence may also be accomplished using other nerves, for example the glossopharyngeal nerve.

The process 1000 then proceeds back to block 1002 where the recording of the iSLN ENG signal continues.

At block 1014, the process 1000 verifies if the IRA meets the criteria defining CSA. For example, in the case where the IRA is the RBI ENG of the iSLN signal, CSA may be defined as peak values remaining below the lower threshold 705 of the range of amplitudes observed during normal respiration as illustrated in FIG. 7. It is to be understood that the definition of CSA will vary depending on the IRA used.

If the IRA meets the criteria of CSA, the process 1000 proceeds to block 1016 where a CSA event is reported. Then, optionally, at block 1018, breathing stimulation may be triggered in response to the detection of the CSA event.

The breathing stimulation acts to replace or augment respiratory drive in response to the CSA event. The stimulation may take a number of different forms and is designed to remain below the arousal threshold of the sleeping subject. Possible targets for stimulation include specific nerves that control respiratory muscles such as, for example, phrenic or intercostal nerves, or their combination. Likewise, direct stimulation of specific muscles that control respiration such as, for example, diaphragm or intercostal respiratory muscles, or their combination, can also used. Treatment can be accomplished by applying stimulation to some or all of the muscles involved in respiration, or to some or all the nerves efferent to these muscles, or some combination of the above. Stimulation of activities of muscles or nerves that increase respiration could be delivered in synchrony with remaining or previous inspiratory activity.

In an alternative embodiment, the stimulation may be aimed at eliciting reflexive and pre-programmed coordinated activity from swallow-related central pattern generators in the central nervous system as previously described at block 1012.

The process 1000 then proceeds back to block 1002 where the recording of the iSLN ENG signal continues.

Optionally, at block 1020, the IRA signal corresponding to normal respiration, the process 1000 terminates any ongoing treatment.

The process 1000 then proceeds back to block 1002 where the recording of the iSLN ENG signal continues.

Figure 14:
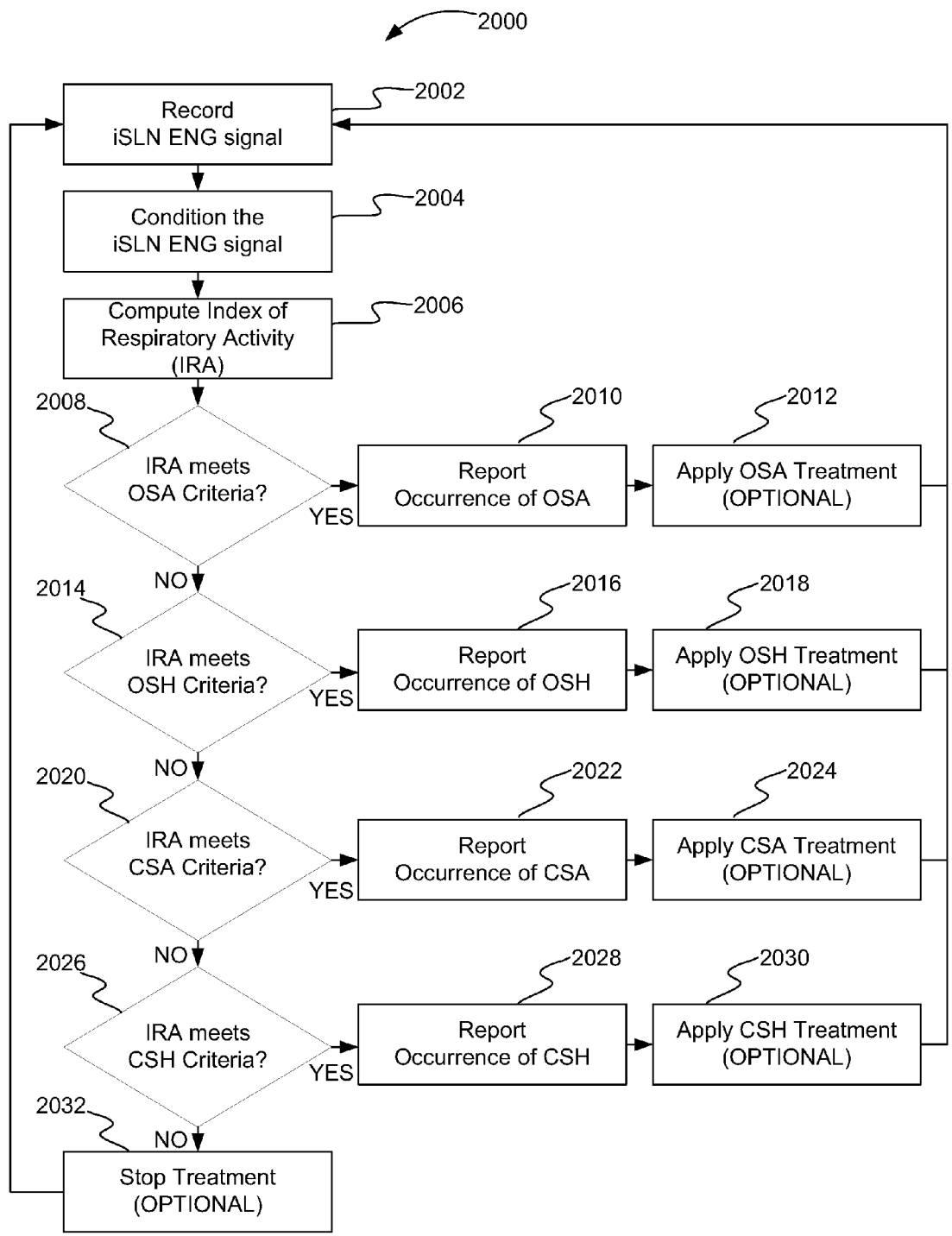
FIG. 14 is a flow diagram depicting the detection, identification and treatment of sleep apnea and hypopnea process in accordance with a second illustrative embodiment of the present invention.

Referring to FIG. 14, there is shown in a flow diagram a process 2000 for the detection and classification of apnea and hypopnea events in accordance with a second illustrative embodiment of the present invention. The steps composing the process are indicated by blocks 2002 to 2032.

The process 2000 starts at block 2002, where the iSLN ENG signal is recorded, after which, at block 2004, the iSLN ENG signal is conditioned (for example amplified).

At block 2006, an index of respiratory activity (IRA) is computed as previously described (see block 1006 of process 1000 from FIG. 13).

At block 2008, the process 2000 verifies if the IRA meets the criteria defining OSA. For example, in the case where the IRA is the RBI ENG of the iSLN signal, the process 2000 verifies if peak values exceed threshold 708 associated with OSA (see FIG. 12).

If the IRA meets the criteria defining OSA, the process 2000 proceeds to block 2010 where an OSA event is reported. Then, optionally, at block 2012, airway opening stimulation as previously described (see block 1012 of process 1000 from FIG. 13) may be triggered in response to the detection of the OSA event.

The process 2000 then proceeds back to block 2002 where the recording of the iSLN ENG signal continues.

At block 2014, the process 2000 verifies if the IRA meets the criteria defining OSH. For example, in the case where the IRA is the RBI ENG of the iSLN signal, the process 2000 verifies if peak values are situated between thresholds 707 and 708 associated with OSH (see FIG. 12).

If the IRA meets the criteria defining OSH, the process 2000 proceeds to block 2016 where an OSH event is reported. Then, optionally, at block 2018, airway opening stimulation as previously described (see block 1012 of process 1000 from FIG. 13), but with adjusted parameters, may be triggered in response to the detection of the OSH event.

The process 2000 then proceeds back to block 2002 where the recording of the iSLN ENG signal continues.

At block 2020, the process 2000 verifies if the IRA meets the criteria defining CSA. For example, in the case where the IRA is the RBI ENG of the iSLN signal, the process 2000 verifies if peak values remain under the threshold 704 associated with CSA (see FIG. 12).

If the IRA meets the criteria defining CSA, the process 2000 proceeds to block 2022 where a CSA event is reported. Then, optionally, at block 2024, breathing stimulation as previously described (see block 1018 of process 1000 from FIG. 13) may be triggered in response to the detection of the CSA event.

The process 2000 then proceeds back to block 2002 where the recording of the iSLN ENG signal continues.

At block 2026, the process 2000 verifies if the IRA meets the criteria defining CSH. For example, in the case where the IRA is the RBI ENG of the iSLN signal, the process 2000 verifies if peak values are situated between thresholds 704 and 705 associated with CSH (see FIG. 12).

If the IRA meets the criteria of CSH, the process 2000 proceeds to block 2028 where a CSH event is reported. Then, optionally, at block 2030, breathing stimulation as previously described (see block 1018 of process 1000 from FIG. 13), but with adjusted parameters, may be triggered in response to the detection of the CSH event.

The process 2000 then proceeds back to block 2002 where the recording of the iSLN ENG signal continues.

It is to be understood that in other alternative embodiments, the detection and classification algorithm may further subdivide the OSH, OSA, CSH and CSA events into multiple severity levels, each level having associated stimulation parameter adjustments.

Neuroprosthesis for the Detection, Identification and Treatment of Sleep Apnea

Figure 15:
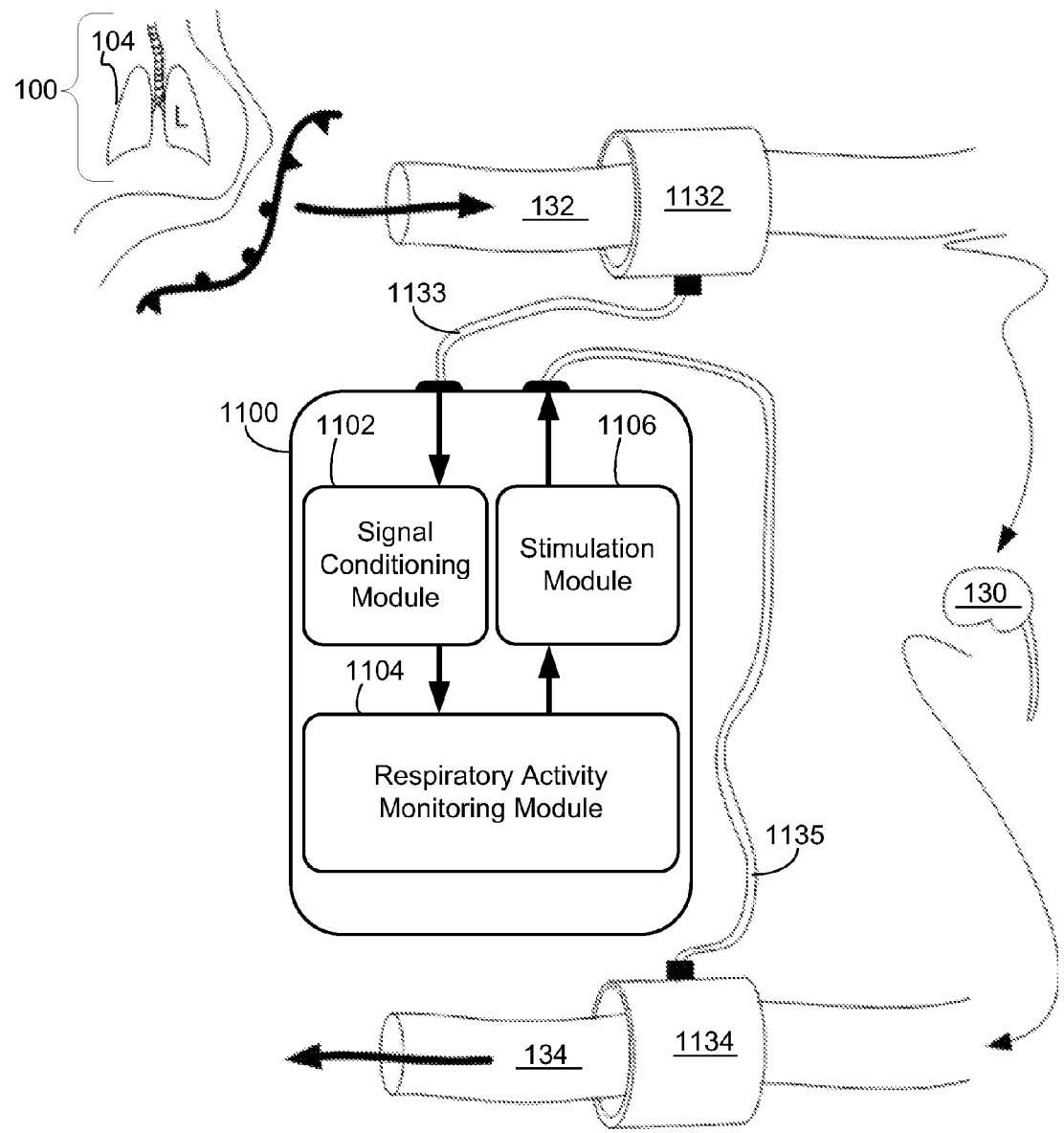
FIG. 15 is a block diagram of an example of a neuroprosthesis for the detection, identification and treatment of sleep apnea.

Referring to FIG. 15, there is shown a block diagram of an example of a neuroprosthesis 1100 for detection, identification and treatment of sleep apnea by monitoring respiratory-related activity from nerve or muscle, interpreting these internal signals to detect and classify adverse events in the airway, and stimulating nerves or muscles to elicit appropriate corrective responses to adverse respiratory events.

In the illustrated example, apnea is detected and identified by monitoring respiratory-related activity from the internal branch of the superior laryngeal nerve (iSLN) 132. The iSLN carries afferents from receptors in the laryngeal mucosa toward the central nervous system 130. Other peripheral nerves carrying afferents modulated by respiratory condition may also be monitored, including the recurrent laryngeal nerve, the main branch of the SLN, the vagus nerve, the phrenic nerve, each nerve alone, or in combination with the other(s). Respiratory activity may also be monitored from nerves carrying efferent signals to muscles of the upper airway, diaphragm, or intercostal muscles, or by monitoring the activity of these respiratory muscles themselves, alone, or in some combination with other nerves or muscles modulated by respiratory activity.

The neuroprosthesis 1100 includes a signal conditioning module 1102, a respiratory activity monitoring module 1104 and a stimulation module 1106.

A recording electrode 1132 is placed in, around, or near a peripheral nerve that carries afferent neural activity from receptors in the upper airway 110 (see FIG. 1) toward the central nervous system 130. One particular nerve that may be used is the iSLN 132. A lead 1133 connects the electrode 1132 to the signal conditioning module 1102.

It is to be understood that depending on the application there may be multiple recording electrodes 1132 to simultaneously or sequentially monitor multiple signal sources. The recording electrode 1132 may also target other peripheral receptors that exhibit modulations of bioelectric potential correlated with respiration. Other receptors that may be monitored to determine respiratory condition include: mechanoreceptors sensitive to positive airway pressure, stretch, position, shear or slip, vibration, texture, touch, touch and pressure, muscle stretch, muscle "drive", air flow, blood pressure or osmolarity; chemoreceptors sensitive to $CO_2$, $O_2$, or pH; thermoreceptors sensitive to temperature or airflow; nociceptors sensitive to polymodal pain, or some combination of the above.

A stimulation electrode 1134 is placed in, around, or near, a target nerve or muscle depending on the type of stimulation used. A lead 1135 connects the stimulation electrode 1134 to the stimulation module 1106. The stimulation electrode 1134 may contain additional features allowing for enhanced current carrying capacity, selective stimulation using current steering, directionally selective stimulation of efferent or afferent fibers, or selectivity for stimulating axons of a particular diameter.

It is to be understood that there may be multiple targets for stimulation and that their selection may vary depending on the identified apneic event and the type of stimulation used. Furthermore, the stimulation may target the central nervous system 130 when the stimulation is aimed at eliciting reflexive and pre-programmed coordinated activity such as swallowing. It is further to be understood that in some alternative embodiments, a single electrode may be used both for the recording 1132 and the stimulation 1134 electrodes, for example when the iSLN is used for both recording and stimulation. Furthermore, multiple electrodes may be use, some or all of them being used both as recording 1132 and stimulation 1134 electrodes while others are used only as recording 1132 or stimulation 1134 electrodes.

In an alternative embodiment, iSLN ENG signals may be passed from electrode 1132 to the signal conditioning module 1102 wirelessly. Similarly, the stimulation signals from the stimulation module 1106 may be passed to the electrode 1134 wirelessly.

The electrodes 1132 and 1134 may be, for example, cuff electrodes. An example of a cuff electrode that may be used as electrodes 1132 and 1134 is disclosed in U.S. Pat. No. 5,824,027 entitled "NERVE CUFF HAVING ONE OR MORE ISOLATED CHAMBERS", issued Oct. 20, 1998, to Hoffer et al. It is to be understood that other types of electrodes, leads, probes, cuff-electrodes, etc., may be used as well. Other examples of cuff electrodes that may be used are disclosed in U.S. Patent Application Publication No. 2008/0065184 entitled "NERVE CUFF, METHOD AND APPARATUS FOR MANUFACTURING SAME", published Mar. 13, 2008, by Hoffer et al. and PCT Patent Application Publication No. WO 2008/025155 entitled "NERVE CUFF INJECTION MOLD AND METHOD OF MAKING A NERVE CUFF", filed Aug. 29, 2007, by Imbeau et al.

The signal conditioning module 1102 conditions the iSLN ENG signal, for example amplifying it, recorded by the first electrode 1132 and provides the conditioned iSLN ENG signal to the respiratory activity monitoring module 1104, which includes an algorithm that uses the conditioned iSLN ENG signal to monitor respiratory activity, detect apnea events before they result in arousal from sleep and identify the type of apnea event.

The signal conditioning module 1102 may include, without limiting the illustrative embodiment to these components, a signal amplifier and a rectifier circuit. Examples of amplifiers and rectifier circuit that may be used are respectively disclosed in U.S. Patent Application Publication No. 2006/0189881 entitled "IMPLANTABLE SIGNAL AMPLIFYING CIRCUIT FOR ELECTRONEUROGRAPHIC RECORDING", published Aug. 24, 2006, by Baru Fassio and U.S. Pat. No. 7,282,980 entitled "PRECISION RECTIFIER CIRCUIT FOR HIGH-DENSITY, LOW-POWER IMPLANTABLE MEDICAL DEVICE", issued Oct. 16, 2007, to Baru Fassio.

The algorithm executed by the respiratory activity monitoring module 1104 implements blocks 1006 to 1010, 1014 and 1016 of process 1000 shown in FIG. 13 or blocks 2006 to 2010 and 2014, 2016, 2020, 2022, 2026 and 2028 of process 2000 shown in FIG. 14. Upon the detection of an apnea event, the respiratory activity monitoring module 1104 sends a trigger to the stimulation module 1106 along with an identification of the type of apnea event, i.e. OSH, OSA, CSH or CSA depending on the implemented algorithm, which generates a stimulation appropriate for the type of apnea event. Optionally, the respiratory activity monitoring module 1104 may also send an indication of the severity level of the apnea event, as well as timing information of previous or continuing respiration patterns, to the stimulation module 1106.

The respiratory activity monitoring module 1104 may optionally provide information about the respiratory activity of the subject, report sleep apnea events and/or allow remote modification of various criteria/thresholds through a communication link such as, for example, a radio frequency (RF) or infrared (IR) link (not shown).

The stimulation module 1106 implements the various stimulation strategies disclosed in blocks 1012 and 1018 of process 1000 and in blocks 2012, 2018, 2024 and 2030 of process 2000, shown in FIGS. 13 and 14, respectively. The produced stimulation signals may be square pulses or arbitrary waveforms, constant voltage or constant current. Stimulation location, amplitude, and/or waveform may be adjusted in a closed-loop based on current respiratory conditions or conditions relayed by the respiratory activity monitoring module 1104 in response to previous stimulation. Stimulation waveforms may also contain features allowing for selective stimulation using current steering, directionally selective stimulation of efferent or afferent fibers, selectivity for stimulating axons of a particular diameter, or features designed to block transmission of undesired bioelectric activity.

The stimulation module 1106 may optionally allow remote selection and/or modification of the stimulation strategies and stimulation parameters through a communication link such as, for example, a radio frequency (RF) or infrared (IR) link (not shown).

The stimulation module 1106 may include, without limiting the illustrative embodiment to this component, a pulse generator for providing current and/or voltage stimulation signals to muscles, nerves or tissue. Examples of pulse generators that may be used are disclosed in U.S. patent application Ser. No. 11/920,814 entitled "IMPLANTABLE PULSE GENERATOR", filed on Oct. 9, 2007, by Roy et al.

Finally, the neuroprosthesis 1100 may include an internal power supply (not shown) or use a transcutaneous energy transfer system (not shown).

Other applications of the invention will be apparent to those skilled in the art. For example, the device has the capacity to detect respiration rate, phase, and timing. This provides for general monitoring of vital signs, aside from apnea detection, and could provide respiration-related parameters to other devices such as external monitoring equipment, or implanted devices such as pacemakers or implantable defibrillators.

Further, apneas occurring during sleep or waking, as in cases of Cheyne-Stokes respiration or Charcot-Marie-Tooth disease could be effectively treated with the invention described herein. Other adverse respiratory conditions or types of sleep disordered breathing could be detected by monitoring naturally occurring receptors in the airway, such as narrowing or obstruction of the airway, snoring, presence of solids or fluids in the airway, respiratory difficulty in congestive heart failure, presence of reflux in the airway, or inappropriate magnitude or timing of airway muscle activity. Detection of these events might be applied to the detection and treatment of respiratory disorders such as asthma, dysphagia, aspiration pneumonia, or SIDS. Stimulation treatments could result in bronchodilation or bronchoconstriction, change in breathing pattern, swallow, cough, gag, muscle or sphincter activation or inhibition, change in mucus or other secretion, or other activity of the airway.

It is to be understood that the various units, modules and sub-modules and algorithms may be implemented using, for example one or more electronic circuit, microcontroller or DSP.

It is also to be understood that the detection, identification and treatment of sleep apnea processes 1000 (see FIG. 13) and 2000 (see FIG. 14) as well as the neuroprosthesis 1100 (see FIG. 15) may be selectively activated, for example when a subject is sleeping. The activation may be user initiated, optionally with a delay, according to a given schedule, by monitoring the heart rate of the subject, the orientation of the subject, etc.

Although the present invention has been described by way of illustrative embodiments and examples thereof, it should be noted that it will be apparent to persons skilled in the art that modifications may be applied to the present particular embodiment without departing from the scope of the present invention.

REFERENCE

[1] Weaver, T. E. and Grunstein, R. R. (2008) "Adherence to Continuous Positive Airway Pressure Therapy: The Challenge to Effective Treatment", Proc Am Thorac Soc Vol 5. pp 173-178

What is claimed is:

1. A method for monitoring the respiratory activity of a subject, comprising the steps of: recording an electroneurogram signal from the internal branch of the superior laryngeal nerve of the subject; conditioning the electroneurogram signal; computing an index of respiratory activity of the conditioned electroneurogram signal; and reporting an occurrence of an apneic event when the index of respiratory activity meets at least one apnea criteria.

2. A method according to claim 1, further comprising the step of generating a stimulation signal which acts to increase airway patency or stimulate breathing following the reporting of the apneic event.

3. A method according to claim 2, wherein parameters of the stimulation signal are selected in accordance with the index of respiratory activity.

4. A method according to claim 2, wherein the stimulation signal is selected so as to elicit a reflexive pattern activity other than coughing from the central nervous system of the subject.

5. A method according to claim 4, wherein the reflexive pattern activity is selected from a group consisting of the negative pressure reflex, yawn reflex, gagging reflex, swallow reflex and any combination thereof.

6. A method according to claim 5, wherein the swallowing reflexive pattern activity is elicited by stimulating the internal branch of the superior laryngeal nerve with an electrical signal at a rate of about 20 Hz to 50 Hz.

7. A method according to claim 5, wherein the swallowing reflexive pattern activity is elicited by stimulating the glossopharyngeal nerve with an electrical signal at a rate of about 20 Hz to 50 Hz.

8. A method according to claim 1, wherein the at least one apnea criteria includes a first criteria associated with obstructive sleep apnea and a second criteria associated with central sleep apnea, and wherein the reporting step includes reporting the apneic event as an obstructive sleep apnea event when the index of respiratory activity meets the first criteria and as a central sleep apnea event when the index of respiratory activity meets the second criteria.

9. A method according to claim 8, further comprising the step of generating a stimulation signal which acts to increase airway patency following the reporting of the obstructive sleep apnea event or stimulate breathing following the reporting of the central sleep apnea event.

10. A method according to claim 8, further comprising the step of reporting an occurrence of an obstructive sleep hypopnea event when the index of respiratory activity meets a third criteria associated with obstructive sleep hypopnea and reporting an occurrence of a central sleep hypopnea event when the index of respiratory activity meets a fourth criteria associated with central sleep hypopnea.

11. A method according to claim 10, further comprising the step of generating a stimulation signal which acts to increase airway patency following the reporting of the obstructive sleep hypopnea event or of the obstructive sleep apnea event, or stimulate breathing following the reporting of the central sleep hypopnea event or of the central sleep apnea event, parameters of the stimulation signal being selected according to whether the obstructive sleep hypopnea event, the obstructive sleep apnea event, the central sleep hypopnea event or the central sleep apnea event was reported.

12. A method according to claim 1, wherein the index of respiratory activity is indicative of the amplitude and timing of the electroneurogram signal.

13. A method according to claim 12, wherein the index of respiratory activity is selected from a group consisting of the peaks of the electroneurogram signal, the root-mean-square of the electroneurogram signal, the peak-to-peak amplitude of the electroneurogram signal, the duration of peaks of the electroneurogram signal, the interpeak intervals of the electroneurogram signal and any combination thereof.

14. A method according to claim 1, wherein the index of respiratory activity is computed by applying a rectification and bin-integration algorithm to the conditioned electroneurogram signal.

15. A method according to claim 14, wherein the step of conditioning the electroneurogram signal includes amplification and band-pass filtering.

16. A method according to claim 14, wherein the step of computing the index of respiratory activity further includes applying a moving average filter to the rectified and bin-integrated amplified electroneurogram signal and optimizing the result.

17. A method according to claim 14, wherein the reporting step includes reporting the apneic event as an obstructive sleep apnea event when the index of respiratory activity exceeding a first threshold.

18. A method according to claim 17, wherein the first threshold is set according to calibration during the normal respiration of the subject during sleep using polysomnographic techniques.

19. A method according to claim 17, further comprising the step of generating a stimulation signal which acts to increase airway patency following the reporting of the obstructive sleep apnea event.

20. A method according to claim 19, wherein a target of the stimulation signal is selected from a group consisting of the hypoglossal nerve, the glossopharyngeal nerve, the genioglossus muscle, the tensor palatini muscle, the sternohyoid muscle and any combination thereof.

21. A method according to claim 20, wherein the target of the stimulation signal comprises fibers in or proximal to a nerve selected from the group consisting of the hypoglossal nerve, the glossopharyngeal nerve, and any combination thereof.

22. A method according to claim 19, wherein a target of the stimulation signal is selected so as to elicit a reflexive pattern activity other than coughing from the central nervous system of the subject.

23. A method according to claim 22, wherein the reflexive pattern activity is selected from a group consisting of the negative pressure reflex, yawn reflex, gag reflex, swallow reflex and any combination thereof.

24. A method according to claim 23, wherein the reflexive pattern activity is swallowing and is elicited by stimulating the internal branch of the superior laryngeal nerve with an electrical signal at a rate of about 20 Hz to 50 Hz.

25. A method according to claim 23, wherein the swallowing reflexive pattern activity is elicited by stimulating the glossopharyngeal nerve with an electrical signal at a rate of about 20 Hz to 50 Hz.

26. A method according to claim 14, wherein the apneic event reporting step includes reporting the apneic event as an obstructive sleep hypopnea event when the index of respiratory activity is between a first and a second thresholds and as an obstructive sleep apnea event when the index of respiratory activity exceeds the second threshold.

27. A method according to claim 26, wherein the first and second thresholds are set according to calibration during the normal and abnormal respiration of the subject during sleep using polysomnographic techniques.

28. A method according to claim 26, further comprising the step of generating a stimulation signal which acts to increase airway patency following the reporting of the obstructive sleep apnea event or of the obstructive sleep hypopnea event, parameters of the stimulation signal being selected according to whether the obstructive sleep apnea event or the obstructive sleep hypopnea event was reported.

29. A method according to claim 28, wherein a target of the stimulation signal is selected from a group consisting of the hypoglossal nerve, the glossopharyngeal nerve, the genioglossus muscle, the tensor palatini muscle, the sternohyoid muscle and any combination thereof.

30. A method according to claim 28, wherein a target of the stimulation signal is selected so as to elicit a reflexive pattern activity other than coughing from the central nervous system of the subject.

31. A method according to claim 30, wherein the reflexive pattern activity is selected from a group consisting of the negative pressure reflex, yawn reflex, gag reflex, swallow reflex and any combination thereof.

32. A method according to claim 31, wherein the reflexive pattern activity is swallowing and is elicited by stimulating the internal branch of the superior laryngeal nerve with an electrical signal at a rate of about 20 Hz to 50 Hz.

33. A method according to claim 31, wherein the swallowing reflexive pattern activity is elicited by stimulating the glossopharyngeal nerve with an electrical signal at a rate of about 20 Hz to 50 Hz.

34. A method according to claim 14, wherein the reporting step includes reporting the apneic event as a central sleep apnea event when the index of respiratory activity remains below a third threshold.

35. A method according to claim 34, wherein the third threshold is set according to calibration during the normal respiration of the subject during sleep using polysomnographic techniques.

36. A method according to claim 34, further comprising the step of generating a stimulation signal which acts to stimulate breathing following the reporting of the central sleep apnea event.

37. A method according to claim 36, wherein a target of the stimulation signal is selected from a group consisting of the phrenic nerve, the intercostal nerve, the diaphragm muscle, the intercostal respiratory muscle and any combination thereof.

38. A method according to claim 36, wherein a target of the stimulation signal is selected so as to elicit a reflexive pattern activity other than coughing from the central nervous system of the subject.

39. A method according to claim 38, wherein the reflexive pattern activity is selected from a group consisting of negative pressure reflex, yawn reflex, gag reflex, swallow reflex and any combination thereof.

40. A method according to claim 39, wherein the reflexive pattern activity is swallowing and is elicited by stimulating the internal branch of the superior laryngeal nerve with an electrical signal at a rate of about 20 Hz to 50 Hz.

41. A method according to claim 39, wherein the swallowing reflexive pattern activity is elicited by stimulating the glossopharyngeal nerve with an electrical signal at a rate of about 20 Hz to 50 Hz.

42. A method according to claim 14, wherein the apneic event reporting step includes reporting the apneic event as a central sleep hypopnea event when the index of respiratory activity is between a third and a fourth thresholds and as a central sleep apnea event when the index of respiratory activity remains under the fourth threshold.

43. A method according to claim 42, wherein the third and fourth thresholds are set according to calibration during the normal and abnormal respiration of the subject during sleep using polysomnographic techniques.

44. A method according to claim 42, further comprising the step of generating a stimulation signal which acts to stimulate breathing following the reporting of the central sleep apnea event or of the central sleep hypopnea event, parameters of the stimulation signal being selected according to whether the central sleep apnea event or the central sleep hypopnea event was reported.

45. A method according to claim 44, wherein a target of the stimulation signal is selected from a group consisting of the phrenic nerve, the intercostal nerve, the diaphragm muscle, the intercostal respiratory muscle and any combination thereof.

46. A method according to claim 37 or claim 45, wherein the target of the stimulation signal comprises fibers in or proximal to a nerve selected from the group consisting of the phrenic nerve, the intercostal nerve, and any combination thereof.

47. A method according to claim 44, wherein a target of the stimulation signal is selected so as to elicit a reflexive pattern activity other than coughing from the central nervous system of the subject.

48. A method according to claim 47, wherein the reflexive pattern activity is selected from a group consisting of the negative pressure reflex, yawn reflex, gag reflex, swallow reflex and any combination thereof.

49. A method according to claim 48, wherein the reflexive pattern activity is swallowing and is elicited by stimulating the internal branch of the superior laryngeal nerve with an electrical signal at a rate of about 20 Hz to 50 Hz.

50. A method according to any one of claim 6, 32, 40, or 49, wherein stimulating the internal branch of the superior laryngeal nerve comprises stimulating fibers of the iSLN in or proximal to the iSLN.

51. A method according to claim 48, wherein the swallowing reflexive pattern activity is elicited by stimulating the glossopharyngeal nerve with an electrical signal at a rate of about 20 Hz to 50 Hz.

52. A method according to claim 7, 33, 41, 51, wherein stimulating the glossopharyngeal nerve in or proximal to the glossopharyngeal nerve.

53. A method according to claim 1, wherein recording an electroneurogram signal from the internal branch of the superior laryngeal nerve of the subject comprises recording from fibers of the iSLN in or proximal to the iSLN.

54. A method for treating sleep apnea or sleep hypopnea in a subject, comprising eliciting a swallow reflex from the central nervous system of the subject following the detection of the sleep apnea or sleep hypopnea, wherein the swallow reflex is elicited by stimulating a nerve with an electrical signal at a rate of about 20 Hz to 50 Hz, wherein the nerve is the internal branch of the superior laryngeal nerve or the glossopharyngeal nerve.

55. A system for monitoring the respiratory activity of a subject, comprising: an electrode configured to be positioned in, around or near the internal branch of the superior laryngeal nerve or its proximal fibers of the subject; a control unit operatively connected to the electrode, the implantable control unit including: a signal conditioning module for conditioning an electroneurogram signal recorded by the electrode; a monitoring and detection module for computing an index of respiratory activity from the electroneurogram signal and for reporting an occurrence of an apneic event when the index of respiratory activity meets at least one apnea criteria.

56. A system according to claim 55, wherein the system is fully implantable.

57. A system according to claim 55, wherein the electrode includes a cuff electrode assembly adapted to surround part of the internal branch of the superior laryngeal nerve of the subject.

58. A system according to claim 57, wherein the cuff electrode assembly is provided with multiple chambers having electrodes therein.

59. A system according to claim 55, wherein the index of respiratory activity is indicative of the amplitude and timing of the electroneurogram signal.

60. A system according to claim 59, wherein the index of respiratory activity is selected from a group consisting of the peaks of the electroneurogram signal, the root-mean-square of the electroneurogram signal, the peak-to-peak amplitude of the electroneurogram signal, the duration of peaks of the electroneurogram signal, the interpeak intervals of the electroneurogram signal and any combination thereof.

61. A system according to claim 55, wherein the index of respiratory activity is computed by applying a rectification and bin-integration algorithm to the conditioned electroneurogram signal.

62. A system according to claim 61, wherein the conditioning module includes an amplifier and a band-pass filter.

63. A system according to claim 61, wherein the monitoring and reporting module reports the apneic event as an obstructive sleep apnea event when the index of respiratory activity exceeding a first threshold.

64. A system according to claim 63, wherein the first threshold is set according to calibration during the normal respiration of the subject during sleep using polysomnographic techniques.

65. A system according to claim 63, further comprising a stimulation electrode and wherein the control unit further includes a stimulation module operatively connected to the monitoring and detection module and to the stimulation electrode, the stimulation module generating through the stimulation electrode a stimulation signal which acts to increase airway patency following the reporting the obstructive sleep apnea event.

66. A system according to claim 61, wherein the monitoring and reporting module reports the apneic event as an obstructive sleep hypopnea event when the index of respiratory activity is between a first and a second thresholds and as an obstructive sleep apnea event when the index of respiratory activity exceeds the second threshold.

67. A system according to claim 66, wherein the first and second thresholds are set according to calibration during the normal and abnormal respiration of the subject during sleep using polysomnographic techniques.

68. A system according to claim 66, further comprising a stimulation electrode and wherein the control unit further includes a stimulation module operatively connected to the monitoring and detection module and to the stimulation electrode, the stimulation module generating through the stimulation electrode a stimulation signal which acts to increase airway patency following the reporting of the obstructive sleep apnea event or of the obstructive sleep hypopnea event, parameters of the stimulation signal being selected according to whether the obstructive sleep apnea event or the obstructive sleep hypopnea event was reported.

69. A system according to claim 61, wherein the monitoring and reporting module reports the apneic event as a central sleep apnea event when the index of respiratory activity remains below a third threshold.

70. A system according to claim 69, wherein the third threshold is set according to calibration during the normal respiration of the subject during sleep using polysomnographic techniques.

71. A system according to claim 69, further comprising a stimulation electrode and wherein the control unit further includes a stimulation module operatively connected to the monitoring and detection module and to the stimulation electrode, the stimulation module generating through the stimulation electrode a stimulation signal which acts to stimulate breathing following the reporting of the central sleep apnea event.

72. A system according to claim 61, wherein the monitoring and reporting module reports the apneic event as a central sleep hypopnea event when the index of respiratory activity is between a third and a fourth thresholds and as a central sleep apnea event when the index of respiratory activity remains under the fourth threshold.

73. A system according to claim 72, wherein the third and fourth thresholds are set according to calibration during the normal and abnormal respiration of the subject during sleep using polysomnographic techniques.

74. A system according to claim 72, further comprising a stimulation electrode and wherein the control unit further includes a stimulation module operatively connected to the monitoring and detection module and to the stimulation electrode, the stimulation module generating through the stimulation electrode a stimulation signal which acts to stimulate breathing following the reporting of the central sleep apnea event or of the central sleep hypopnea event, parameters of the stimulation signal being selected according to whether the central sleep apnea event or the central sleep hypopnea event was reported.

75. A system according to claim 55, wherein the control unit further includes a stimulation module operatively connected to the monitoring and detection module, the stimulation module generating through the electrode a stimulation signal which acts to increase airway patency or stimulate breathing following the reporting of the apneic event.

76. A system according to claim 75, wherein parameters of the stimulation signal are selected by the stimulation module in accordance with the index of respiratory activity.

77. A system according to claim 75, wherein the stimulation signal is generated by the stimulation module so as to elicit a reflexive pattern activity other than coughing from the central nervous system of the subject.

78. A system according to claim 77, wherein the reflexive pattern activity is selected from a group consisting of the negative pressure reflex, yawn reflex, gag reflex, swallow reflex and any combination thereof.

79. A system according to claim 78, wherein the swallowing reflexive pattern activity is elicited by generating an electrical signal at a rate of about 20 Hz to 50 Hz.

80. A system according to claim 75, wherein the at least one apnea criteria includes a first criteria associated with obstructive sleep apnea and a second criteria associated with central sleep apnea, and wherein the monitoring and detection module reports the apneic event as an obstructive sleep apnea event when the index of respiratory activity meets the first criteria and as a central sleep apnea event when the index of respiratory activity meets the second criteria.

81. A system according to claim 80, wherein the stimulation module generates through the electrode a stimulation signal which acts to increase airway patency following the reporting of the obstructive sleep apnea event.

82. A system according to claim 80, wherein the monitoring and detection module reports an occurrence of an obstructive sleep hypopnea event when the index of respiratory activity meets a third criteria associated with obstructive sleep hypopnea and an occurrence of a central sleep hypopnea event when the index of respiratory activity meets a fourth criteria associated with central sleep hypopnea.

83. A system according to claim 82, wherein the stimulation module generates through the electrode a stimulation signal which acts to increase airway patency following the reporting of the obstructive sleep hypopnea event or of the obstructive sleep apnea event, parameters of the stimulation signal being selected according to whether the obstructive sleep hypopnea event or the obstructive sleep apnea event was reported.

84. A system according to claim 75, further comprising a stimulation electrode operatively connected to the stimulation module, and wherein the stimulation signal is generated through the stimulation electrode.

85. A system according to claim 84, wherein parameters of the stimulation signal are selected by the stimulation module in accordance with the index of respiratory activity.

86. A system according to claim 84, wherein the stimulation signal is generated by the stimulation module so as to elicit a reflexive pattern activity other than coughing from the central nervous system of the subject.

87. A system according to claim 86, wherein the reflexive pattern activity is selected from a group consisting of the negative pressure reflex, yawn reflex, gag reflex, swallow reflex and any combination thereof.

88. A system according to claim 87, wherein the swallowing reflexive pattern activity is elicited by generating an electrical signal at a rate of about 20 Hz to 50 Hz.

89. A system according to claim 84, wherein the at least one apnea criteria includes a first criteria associated with obstructive sleep apnea and a second criteria associated with central sleep apnea, and wherein the monitoring and detection module reports the apneic event as an obstructive sleep apnea event when the index of respiratory activity meets the first criteria and as a central sleep apnea event when the index of respiratory activity meets the second criteria.

90. A system according to claim 89, wherein the stimulation module generates through the stimulation electrode a stimulation signal which acts to increase airway patency following the reporting of the obstructive sleep apnea event or stimulate breathing following the reporting of the central sleep apnea event.

91. A system according to claim 84, wherein the monitoring and detection module reports an occurrence of an obstructive sleep hypopnea event when the index of respiratory activity meets a third criteria associated with obstructive sleep hypopnea and an occurrence of a central sleep hypopnea event when the index of respiratory activity meets a fourth criteria associated with central sleep hypopnea.

92. A system according to claim 91, wherein the stimulation module generates through the stimulation electrode a stimulation signal which acts to increase airway patency following the reporting of the obstructive sleep hypopnea event or of the obstructive sleep apnea event, or stimulate breathing following the reporting of the central sleep hypopnea event or of the central sleep apnea event, parameters of the stimulation signal being selected according to whether the obstructive sleep hypopnea event, the obstructive sleep apnea event, the central sleep hypopnea event or the central sleep apnea event was reported.

93. A system according to claim 84, wherein the stimulation electrode is configured to be positioned in, around or near the glossopharyngeal nerve of the subject or its proximal fibers.

94. A system according to claim 93, wherein the stimulation electrode includes a cuff electrode assembly adapted to surround part of the glossopharyngeal nerve of the subject.

95. A system according to claim 93, wherein the stimulation signal is generated by the stimulation module so as to elicit a reflexive pattern activity other than coughing from the central nervous system of the subject.

96. A system according to claim 95, wherein the reflexive pattern activity is selected from a group consisting of the negative pressure reflex, yawn reflex, gag reflex, swallow reflex and any combination thereof.

97. A system according to claim 96, wherein the swallowing reflexive pattern activity is elicited by generating an electrical signal at a rate of about 20 Hz to 50 Hz.

98. A system for treating a sleep apnea event, comprising: a sleep apnea event detection module; a stimulation electrode configured to be positioned in, around or near the internal branch of the superior laryngeal nerve or the glossopharyngeal nerve of the subject or its proximal fibers; and a stimulation module operatively connected to the detection module and to the electrode; wherein following a detection of the sleep apnea event by the detection module, the stimulation module generates through the stimulation electrode a stimulation signal having a rate of about 20 Hz to 50 Hz in order to elicit a swallowing reflexive pattern activity.

99. A system according to claim 98, wherein the system is fully implantable.

100. A system according to claim 98, wherein the stimulation electrode includes a cuff electrode assembly adapted to surround part of internal branch of the superior laryngeal nerve or the glossopharyngeal nerve of the subject or its proximal fibers.

* * * * *